United States Patent [19]

Coatney

[11] Patent Number: 4,707,138

[45] Date of Patent: Nov. 17, 1987

[54] COLOR MEASURING AND CONTROL DEVICE

[75] Inventor: Charles W. Coatney, Reno, Nev.

[73] Assignee: Filper Industries, Inc., Reno, Nev.

[21] Appl. No.: 740,622

[22] Filed: Jun. 3, 1985

[51] Int. Cl.⁴ .......................... G01J 3/46; G01N 21/27
[52] U.S. Cl. .................................... 356/402; 250/226; 356/445
[58] Field of Search ............... 356/445, 402, 407, 429, 356/431, 243; 250/226

[56] References Cited

U.S. PATENT DOCUMENTS

| | | | |
|---|---|---|---|
| 1,917,379 | 7/1933 | Lowry | 356/429 |
| 3,890,049 | 6/1975 | Collins et al. | 356/445 X |
| 3,998,555 | 12/1976 | Babb | 356/402 |
| 4,031,752 | 6/1977 | Sanders | 356/429 X |
| 4,057,352 | 11/1977 | Babb | 356/402 |
| 4,259,020 | 3/1981 | Babb | 356/402 |
| 4,435,093 | 3/1984 | Krause et al. | 356/43 X |
| 4,486,098 | 12/1984 | Buchegger et al. | 356/445 |
| 4,498,778 | 2/1985 | White | 356/243 X |
| 4,553,847 | 11/1985 | Lang | 356/445 |
| 4,591,996 | 5/1986 | Vachon | 356/35.5 X |

Primary Examiner—Vincent P. McGraw
Attorney, Agent, or Firm—Gerald L. Moore

[57] ABSTRACT

A color detecting device comprising a head (14) supported on an arm (30) for oscillatory motion over the product (11) being color measured to render a signal responsive to the average color of the product. A height detector (44) provides a signal indicating the distance between the product and head and is used to modify the color signal accordingly. A temperature sensor (39) in the head indicates an overtemperature condition for causing movement of the head away from the product. The screen (17) transparency is measured by the indicator (47, 48) to indicate when the screen is dirty.

2 Claims, 4 Drawing Figures

COLOR MEASURING AND CONTROL DEVICE

FIELD OF THE INVENTION

A device for detecting the color of articles by directing different wavelengths of light, such as red and green, thereon and detecting the reflected light to measure the color of the articles.

BACKGROUND OF THE INVENTION

This invention relates primarily to apparatus especially useful in the controlling of continuously operating processing machinery such as equipment for blanching or roasting of peanuts, french fried potatoes, or for peeling potatoes and the like. In such controlled processes, the color of the product is detected as it leaves the processing area. Since the color changes with the degree of processing such as heating, blanching, peeling and the like, detection of the product color can be relied upon to indicate whether the procedure is satisfactory. Thereafter, the timing or temperature usually can be altered to optimize the process. Past color detectors have included a light emitting head which is stationary over the product. The product is carried by a conveyor through a heating oven or the like and thereafter beneath the head of the color detector. Because the product is heated and in the process of being cooked it gives off various gases and radiates heat. If the color detecting head is exposed to an overtemperature condition or if vapor carried matter collects on the lens it can be rendered inoperative.

Because the product is stacked on a conveyor for movement through a heating processor, the distance between the head and the product can vary due to changes in the depth of the product on the conveyor. This variance in spacing between the head and the product, as well as the degree to which the conveyor is covered by the product, can change significantly the detected color. Thus, in the case of the processor being controlled by a signal responsive to this color, erroneous control signals are generated.

It is the purpose of the present invention to provide an improved device for reading the color of a product.

SUMMARY OF THE INVENTION

An apparatus for measuring the color of a product supported on a substantially horizontal surface comprising a head with means for directing light, usually in the red and green or possibly blue wavelength regions, onto the product and means for detecting the light reflected from the product. The reflected light is changed to an electronic signal indicating the color of the product.

To obtain an average color, the head is translated along a horizontal path back and forth above the product. Means are provided within the head for measuring the temperature thereof and if the temperature exceeds a predetermined limit, an emergency circuit is triggered to move the head away from the product so it will not become overheated and damaged. The temperature measured is also used to compensate the color indicating signal to make it more accurate.

Additionally, a height measuring device is incorporated in the head to detect the distance between the head and the product. An electrical signal indicating this distance is used to modify the color indicating signal to also make it more accurate and delete any variances due to a change in the distance between the head and product. A special combination of light sources and lens is also provided to maximize the effective viewing area. The light sources and lens are temperature controlled and maintained clear of foreign matter to enhance the life and accuracy of the apparatus.

DESCRIPTION OF THE INVENTION

FIG. 1 is a perspective view of a color measuring device incorporating the present invention.

FIG. 2 is a block diagram showing the electronic components of the invention,

FIG. 3 shows the manner in which the color measuring head is actuated across the product; and FIG. 4 is a cross sectional view of the color detector head.

DESCRIPTION OF THE DRAWINGS

Apparatus incorporating the subject invention is shown in FIG. 1 wherein a conveyor 10 carries the product 11, usually a food product, from an oven or other form of processing station past a color measuring apparatus 12. The color measuring apparatus tests the color of the product as it passes and while not shown in the drawing, a signal therefrom is used to adjust the process so the color falls within a predetermined range thereby indicating that a proper processing procedure is being achieved. Usually the temperature or belt speed is adjusted to optimize the process.

The product is tested by exposing it to light in a predetermined frequency range or ranges. The reflected light is then measured to determine the color of the product in those ranges. For this purpose a head 14 is suspended over the product such that light sources 15 and 16 are positioned to direct light down on the conveyor (FIG. 4). The head comprises a housing 16 preferably made of opaque material and with a bottom wall 17 including a transparent window 17A. By proper energization, light in predetermined frequency ranges, such as red and green is directed onto the product with the reflected light passing back through an aspheric lens 18A in an optical system 18 contained in a light proof enclosure 19. The light is transmitted through a dichroic reflector 20 or other means which separates the light ranges by passing light in one range and reflecting light in another range. Separation of the light ranges can also be accomplished by use of fiber optics, etc. Thus, the separated red and green ranges are represented by the arrows 21 and 22 respectively, with an electrical signal being generated responsive thereto by the respective photodiodes 24 and 25. The electrical signal generated by the photodiodes is responsive to the magnitude of light in each range and thus indicates the color of the product in these light frequencies. For a more complete description of the operation of this portion of a typical system, reference can be made to U.S. Pat. No. 4,057,352, Color Grading Apparatus Utilizing Infra-red Light Source, issued on Nov. 8, 1977.

One of the problems with prior art devices is the inability to gain an accurate average reading for the width of the product passing thereby. If the head is raised sufficiently to view the overall product width it is usually far enough from the product to allow other variances such as ambient light, etc, to affect the reading. If the head is placed closer to the product a smaller area is viewed and a less than average reading is gained. The subject invention allows for an average reading to be achieved for the total width of the product stream. Another problem encountered in prior art devices is the damaging of the detecting head by overtemperature conditions. Also, fumes frequently rise from the heated product and fog up the optical components of a detecting head and, if not remedied, will result in faulty readings being obtained.

Figure 1:
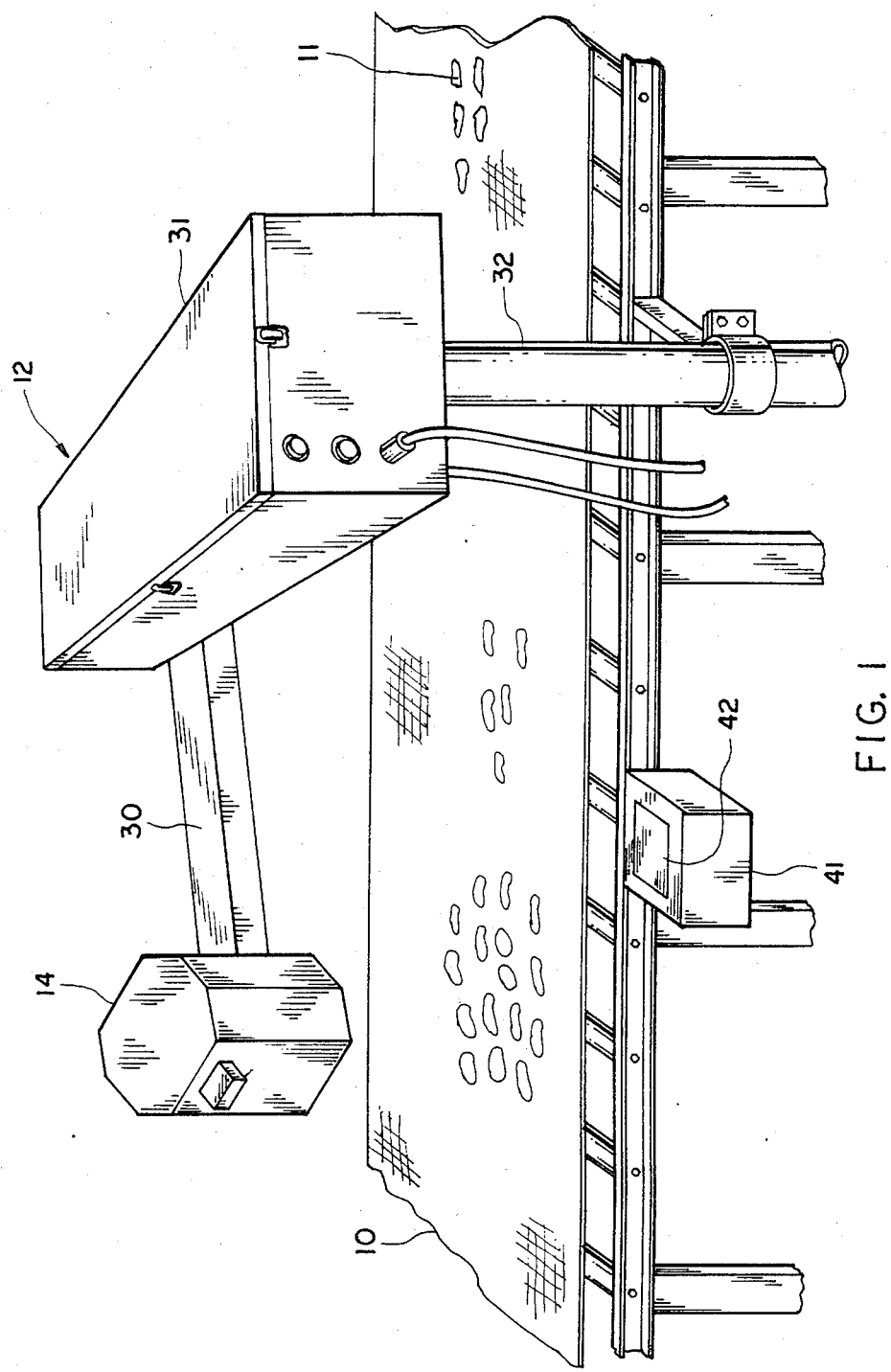
Figure 3:
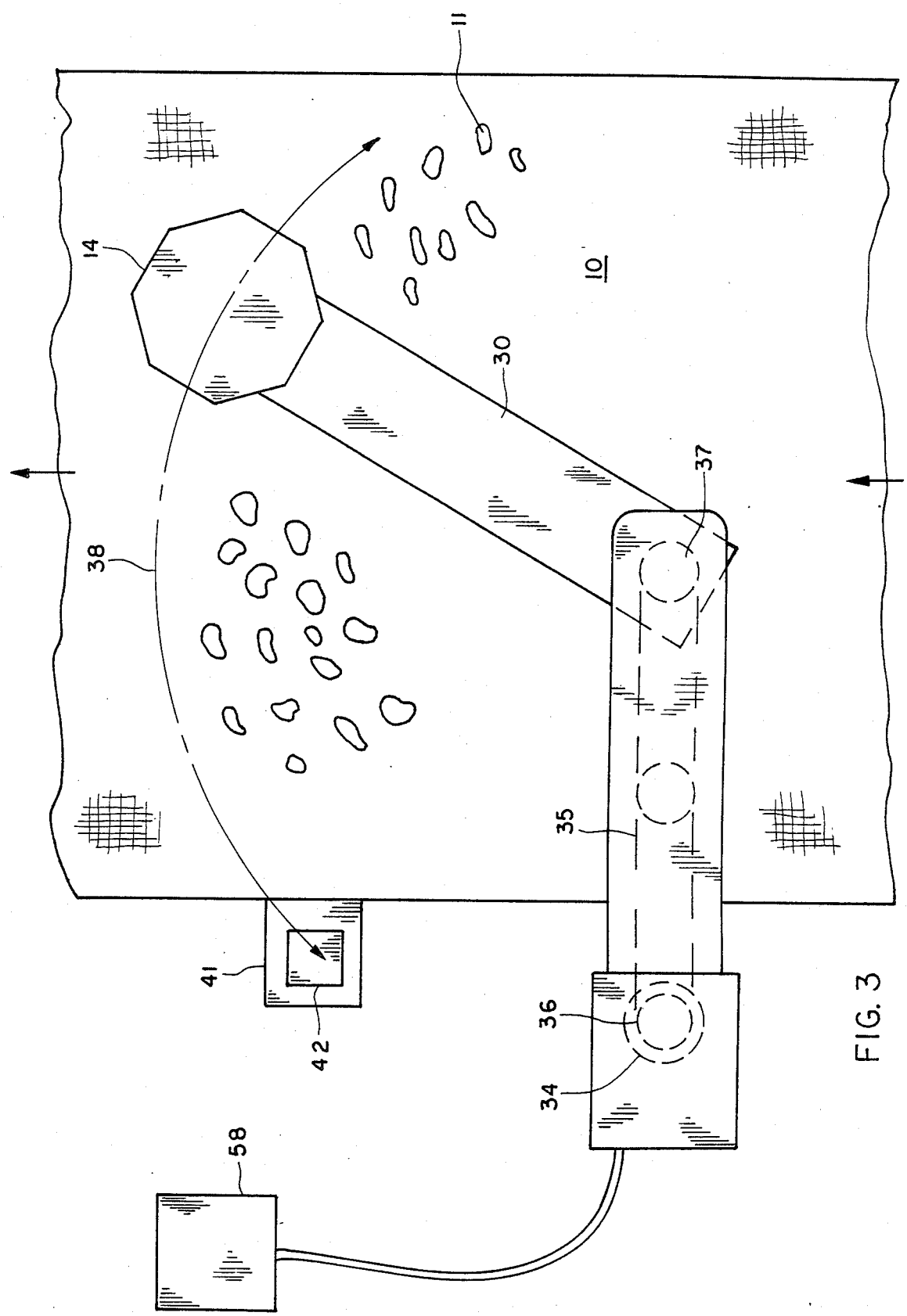

In accordance with the present invention, the head is traversed across the product as the product is moved past and for that purpose, is mounted on a supporting arm 30 (see FIGS. 3 and 4) which is pivotally attached to a second arm 31. The arm 31 is attached at one end to the top of a standard 32 (FIG. 1) extending vertically and adjacent the conveyor 11. Preferably the arm 31 extends to the mid-portion of the conveyor and the arm 30 is slightly longer than one half the width of the conveyor to allow the head 14 to be traversed across the complete width of the belt. A drive motor 34 positioned the top of the standard drives chain or belt 35 extending around a sprocket 36 on the drive motor and a second sprocket 37 fixed fixed to the supporting spindle 30A of the arm 30. By driving the belt 35 the arm 30 can be actuated to swing the head 14 through an arcuate path indicated by the dotted line 38 (FIG. 3) across the width of the conveyor belt. By oscillation of the arm to move the head across the belt continuously, an average color reading of the product can be achieved since the head traverses the width of the product stream as the stream proceeds past the head. Other supports for the head will achieve equal results as long as the head is traversed across the products preferably in a continuous motion.

As an added feature of the invention there is located within the head one or more temperature sensors 39 which indicate the temperature to which the head is heated. When an overtemperature condition exists for the head, a signal is transmitted back to the control to actuate the motor 34 and move the head immediately over a pad 40 spaced (FIG. 3) laterally from the conveyor belt. In this manner the head is removed from the immediate proximity of the product and the overtemperature condition is alleviated before the head is damaged.

As a second feature of the invention, the device is calibrated while in the position laterally spaced from the conveyor and such calibration is affected periodically to assure accurate readings. Calibration is achieved by positioning one or more color calibrating targets 42 (FIG. 3) beside the conveyor on a holder 41 over which the head can be positioned periodically. With the head so positioned calibration can then be achieved in a suitable manner such as is described in U.S. Pat. No. 4,259,020 entitled Automatic Calibration Control for Color Grading Apparatus issued on Mar. 31, 1981.

Another feature of the invention allows for the detection of ambient light and adjustment of the readant signal from the color detecting system responsive to the level of ambient light. For this purpose a light detector 43 is provided for detecting the ambient light surrounding the head 14. By generating a signal responsive to this ambient light and using that ambient light signal to modify the product color signal a more accurate indication of the product is generalized.

In accordance with another feature of the invention the height of the head above the product is constantly measured so as to provide for modification of the color signal to accommodate changes in height. For this purpose a sonic measuring device 44 (FIG. 4) is fixed to the head 14 to provide a signal indicative of the distance between the product and the head. One device which functions satisfactorily in this manner is the Polaroid Sonic Position Measuring device which is available commercially. With the signal provided by this device the color signal is reduced or increased depending upon the variance in the height of the head from a normal or predetermined height above the product. The depth of the product on the conveyor changes this height. The measuring device preferably has a long time constant so as to average the height as the head translates across the conveyor.

Figure 4:
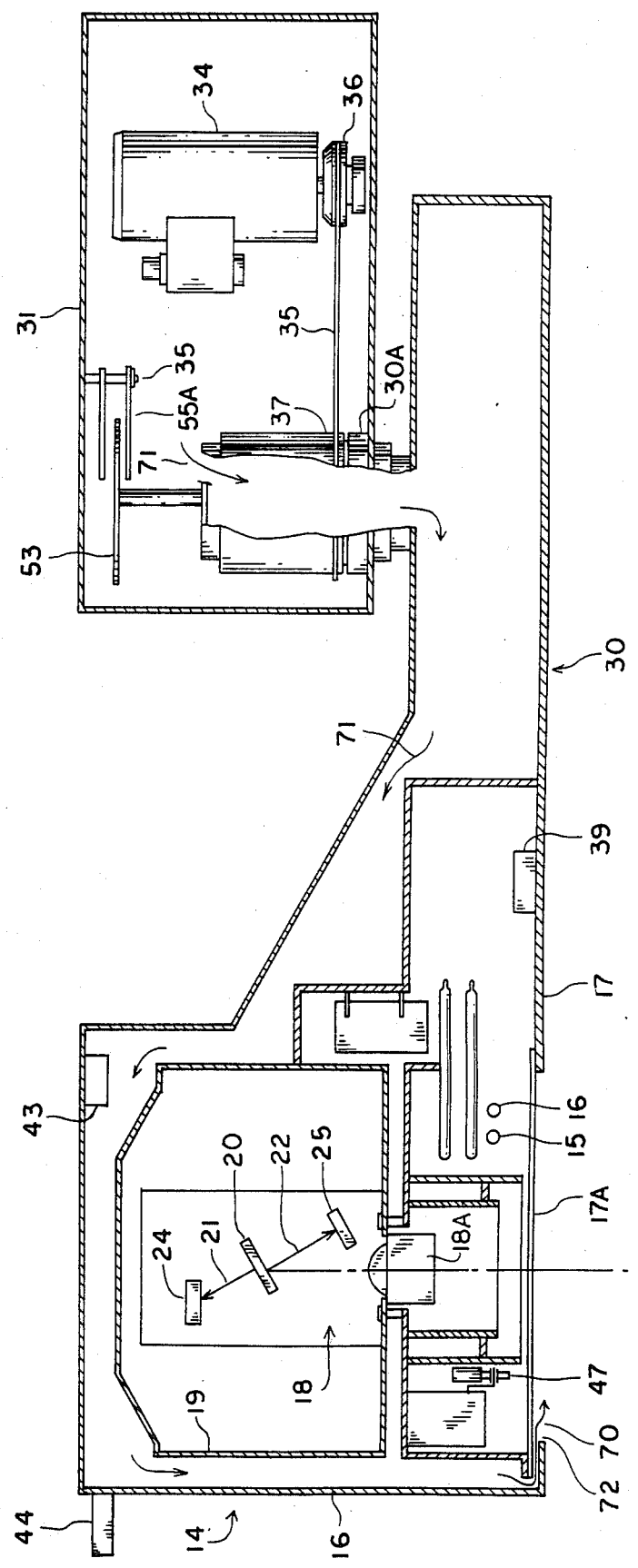

In accordance with another feature of the invention there is provided a lens sensor which senses the accumulation of foreign matter on the screen 17 of the head. For this purpose a light detector 47 is positioned within the head 14 (FIG. 4). The light detector supplies a signal indicating the light from the source 15 and 16 reflected back from the transparent window 17A Thus as dust and the like accumulates on the to diminish the transparency of the screen the reflected light increases to a predetermined amount causing when an alarm signal to be sounded indicating that the screen should be cleaned.

Figure 2:
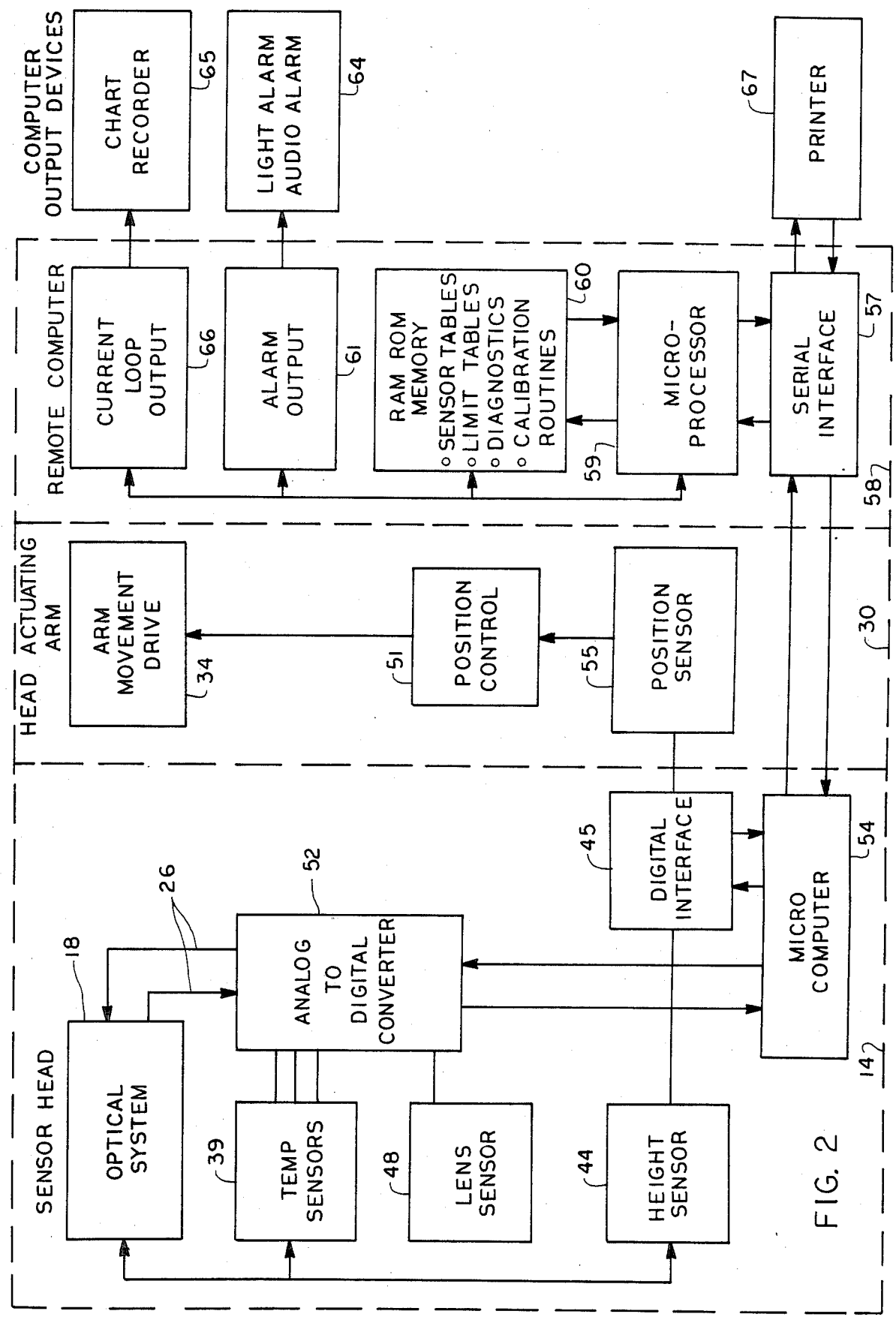

Illustrated in FIG. 2 is a block diagram of the electrical circuit of the subject invention. The sensor head 14 is supported by the actuating arm 30 and driven by the oscillator drive 34 which is under control of a position control 51. The signals from the sensor head are fed through the conductors 26 to an analog to digital converter 52 which has the primary function of transposing the analog signals to digital form for proper processing in a micro computer 54. The signal from the height sensor 44 is fed through the digital interface 45 to this computer as well as. The signals from the temperature sensor and the lens sensor 48. Each of these signals is utilized to modulate or modify the primary signal received from the sensor head optical system. The head sensor signal also serves to detect operational limits beyond which the head signal should not be utilized.

The micro computer 54 joins these signals for the purpose of generating a composite signal reflecting the respective input from those modifying conditions. The arm position sensor 55 for detecting the general position of the head relative to the conveyor is shown in FIG. 4. This sensor comprises a disk 53 fixed to rotate with the spindle 30A to indicate the physical positioning of the arm 30 relative to the arm 31. An optical system 55A detects the rotative position of the disk in any of several well known methods and supplies a signal which is compared with that of the microcomputer to indicating a desired positio generate a signal for energizing the oscilator drive 34. The position control 51 thereby regulates the drive 34 for oscillating and positioning the sensor head 14. A similar system is provided for the arm 31.

The output from the microcomputer 54 is fed to a microcomputer 58 including the serial interface 57 and a micro processor 59. The computer 58 includes a series of limit and sensor tables 60 which receive the height, temperature and dirt sensor signals and by use of a standard table look-up program, supplies a modifying signal, where apropriate, to alter the color signal received from the sensor head 14. Limits are also provided by the limit detector 60 which includes limits for the temperature sensor 39 and the lens sensor 48. If such limits are exceeded an alarm 64 is energized by an alarm output circuit 61. Additionally, a diagnostic control is energized to analyze the system in the usual manner. As described before, the calibration circuit 66 is also provided and a chart recorder 65 energized by a current loop output circuit 66, and a printer 67 provide printouts of the operation of the color measuring and control device. Also the microprocessor 59 can supply a signal to regulate the processor (not shown) that is processing the product on the conveyor.

In the manner described, there is provided a color detector which senses the overall color of the product passing on the conveyor for generation of a signal which ultimately is utilized for process control, etc. This signal can be modified by the varying height of the detector head relative to the product. Other variables such as the temperature of the head and the dirt deposits on the head screen are also detected to indicate when remedial action should be taken.

Additional measures are also taken to provide an accurate indication of the product color. A film of air is blown along the lower face of the transparent screen 17A as indicated by the arrow. This air is circulated through the arms 31 and 30 for cooling the electronic and mechanical components therein as indicated by the arrows 71. The air originates at a pressured air source (not shown) and after passage through the arms, flows around the housing 19 and out of the port 72 adjacent the transparent screen. Thus the circulated air is used for the dual purpose of cooling the device and sweeping contaminated fumes from the vicinity of the screen.

I claim:

1. A color sensor for detecting the color of a product carried on a top surface of a support, said sensor comprising:
    means to generate a light beam including selected color wavelengths,
    a head for transmitting said light beam onto said product,
    means supporting said head for translating movement over said support top surface along a path generally parallel to said top surface,
    detector means in said head for detecting the reflected light from said product,
    means to analyze said reflected light to generate an output signal responsive to the color of said product;
    means for generating a distance signal responsive to the distance between the product and said head, and
    means to modulate said output signal responsive to said distance signal to adjust for light changes due to changes in the distance between the product and the head.

2. A color sensor for detecting the color of a product carried on the top surface of a support, said sensor comprising:
    a color sensing head including means for directing light of a predetermined wavelength onto said product;
    a first arm supporting at one end said color sensing head,
    a second arm rotatably fixed at one end to the other end of said first arm,
    means rotatably supporting said second arm other end; and,
    means for rotating said first arm to oscillate said head back and forth over said support to detect an average color of said product.

* * * * *